United States Patent [19]
Wolf

[11] Patent Number: 5,496,536
[45] Date of Patent: Mar. 5, 1996

[54] PERCUTANEOUS LYMPHOGRAPHY

[76] Inventor: Gerald Wolf, 5 Hawthorne Rd., Winchester, Mass. 01890

[21] Appl. No.: 428,558

[22] Filed: Apr. 25, 1995

Related U.S. Application Data

[63] Continuation of Ser. No. 128,344, Sep. 28, 1993, abandoned, which is a continuation of Ser. No. 855,570, Mar. 23, 1992, abandoned, which is a division of Ser. No. 530,034, May 29, 1990, Pat. No. 5,114,703, which is a continuation-in-part of Ser. No. 358,678, May 30, 1989, abandoned.

[51] Int. Cl.$^6$ .............................. A61B 5/055; A61B 8/13
[52] U.S. Cl. ...................... 424/9.322; 424/9.5; 424/9.37; 514/715; 514/723; 514/832; 514/937; 514/941; 514/943; 436/173
[58] Field of Search ................. 424/9.322, 9.5; 514/492, 502, 715, 723, 832, 937, 938, 941, 943; 128/653.4, 654, 662.02; 436/173

[56] References Cited

U.S. PATENT DOCUMENTS

| | | | |
|---|---|---|---|
| 3,818,229 | 6/1974 | Long, Jr. | 252/478 |
| 3,975,512 | 8/1976 | Long, Jr. | 424/5 |
| 4,073,879 | 2/1978 | Long, Jr. | 424/5 |
| 4,105,798 | 8/1978 | Moore et al. | 514/756 |
| 4,146,499 | 3/1979 | Rosumo | 252/186.32 |
| 4,225,725 | 9/1980 | Hoey | 560/37 |
| 4,367,216 | 1/1983 | Mutzel et al. | 424/5 |
| 4,397,870 | 8/1983 | Sloviter | 514/672 |
| 4,404,182 | 9/1983 | Vermess et al. | 424/5 |
| 4,451,251 | 5/1984 | Osterholm | 604/24 |
| 4,452,773 | 6/1984 | Molday | 424/1.1 |
| 4,735,210 | 4/1988 | Goldenberg | 128/654 |
| 4,770,183 | 9/1988 | Groman et al. | 128/654 |
| 4,795,698 | 1/1989 | Owen et al. | 435/4 |
| 4,827,945 | 5/1989 | Groman et al. | 128/653.4 |
| 4,865,836 | 9/1989 | Long | 424/5 |
| 5,160,725 | 11/1992 | Pilgrim | 424/9 |

FOREIGN PATENT DOCUMENTS

| | | |
|---|---|---|
| 1044917 | 4/1985 | European Pat. Off. . |
| 0208531 | 7/1986 | European Pat. Off. . |
| 0220153 | 10/1986 | European Pat. Off. . |
| 0231091 | 1/1987 | European Pat. Off. . |
| 0231070 | 5/1987 | European Pat. Off. . |
| 0307087 | 8/1988 | European Pat. Off. . |
| 4225413 | 12/1967 | Japan . |
| 9046230 | 9/1982 | Japan . |
| 0166626 | 2/1984 | Japan . |
| 9067229 | 4/1984 | Japan . |
| 0615344 | 1/1980 | Switzerland . |
| 880060 | 1/1988 | WIPO . |
| 9001899 | 3/1990 | WIPO . |
| 9101149 | 2/1991 | WIPO . |
| 9101148 | 2/1991 | WIPO . |
| 9101147 | 2/1991 | WIPO . |

OTHER PUBLICATIONS

Bergqvist, et al. Sem. Nucl. Med XIII: 9 (1983).
Ege, Sem. Nucl. Med XIII: 26 (1983).
Weinstein, et al. Science 208: 1334: (1982).
Long, et al. Radiology 133: 71 (1979).
Elmore, et al. Physical Review (2d series) 54: 309–310 (1938).
McNab, et al. J. Appl. Phys. 39: 5703 (1968).
Molday, et al. J. Immuno. Meth. 52: 353 (1982).
Hnatowich, et al. Science 220: 613 (1983).
Beisbarth, et al. Proc. 5th Int'l Sympos. on Perfluor. Blood Subst.: 3 (Mar. 1981).
Persico, et al. J. Org. Chem. 50: 5156 (1985).
Sharts, et al. J. of Fluorine Chem. 11: 637 (1978).
Davis, Advances in Clin. Nutrition Chp. 19, MTP Press: (1982), pp. 213–239.
Yokoyama, et al. Fed. Proc. 34: 1478 (1975).
Steiner, et al. J. Clin. Invest. 57: 732 (1976).
Pandolfe, et al. Am. Inst. Chem. Eng. presentation (1983).
Chandonnet, et al. SOAP/COSMETICS/CHEM. SPEC: 37 (1985).
Korstvedt, et al. American Paint & Coatings Jnl.: 38 (1985).
Korstvedt, et al. Drug and Cosmetic Industry: (Nov. 1984).
Microfluidics Corp. Prepared Foods: 171 (Mar. 1985).
Gaulin Corporation, Technical Bulletin #67: (Sep. 1982).
Alliger, American Laboratory: (Oct. 1985).
Berliner, et al., Biotechnology Laboratory: 46 (Mar. 1984).
Gould, et al. J. of Trauma 23: 720 (1983).
Police, et al. Critical Care Medicine 13: 96 (1985).
Nunn, et al. Am. J. Cardiology 52: 205 (1983).
Bose, et al. Brain Research 328: 223 (1985).
Spears, et al. Circ. Abst. 68 Supp. III: 317 (1983).
Patel, et al. Fed. Proc. 29: 1740 (1970).
Itoh, et al. Gan to Kagaku Ryoho 11: 864 (1984).
Peck, et al. Investigative Radiology 2: 129 (1984).
Dobben, et al. Neuroradiology 6: 17 (1973).
Brahme, et al. Acta Radiologica Suppl. 347: 459 (1975).
Liu, et al. Investigative Radiology 11: 319 (1976).
Long, et al. Radiology 105: 323 (1972).
Riess, Artifical Organs 8: 44 (1984).
Riess, Proc. Int'l Symp. Blood Subst.: 135 (1987).
Moss, et al. Biomat. Art. Cells Art. Org. 15(2): 333 (1987).
Geyer, Biomat. Art. Cells Art. Org. 15(2): 329 (1987).
Rockwell, Biomat. Art. Cells Art. Org. 15(2): 430 (1987), (Abstract Only).
Long, et al., Biomat. Art. Cells Art Org. 15(2): 417 (1987), (Abstract Only).
Long, et al. Biomat. Art. Cells Art. Org. 15(2): 418 (1987).
Arlen, et al. Biomat. Art. Cells Art. Org. 15(2): 431 (1987).
Burgan, et al. Biomat. Art. Cells Art. Org. 15(2): 403 (1987).
Strand, et al. J. Nucl. Med. 20: 1038 (1979).
Mikheev, Atomic Energy Rev. 14: 1 (1976).
Weissleder, et al. Radiology 175: 489–498 (1990).
File Server Derwent, File Wpil, accession no. 84–206321 [33], Derwent Publications Ltd. London, G.B. Amosov et al. (1979).

*Primary Examiner*—Gary E. Hollinden
*Attorney, Agent, or Firm*—Knobbe, Martens, Olson & Bear

[57] ABSTRACT

Injectable contrast agents of great clinical importance for lymphography, characterized by non-water soluble particle sizes between about 5 or 10 nm and about 500 or 900 nm, which have selective distribution to lymph nodes upon percutaneous administration and can be imaged with millimeter resolution. Also disclosed are methods for performing percutaneous lymphography using these contrast agents.

9 Claims, No Drawings

PERCUTANEOUS LYMPHOGRAPHY

RELATION TO RELATED APPLICATION

This application is a continuation of application Ser. No. 08/128,344, filed Sep. 28, 1993, abandoned, which is a continuation of U.S. application Ser. No. 07/855,570 filed Mar. 23, 1992, abandoned which is a divisional of U.S. application Ser. No. 07/530,034 filed May 29, 1990, now U.S. Pat. No. 5,114,703, which is a continuation-in-part of U.S. application Ser. No. 07/358,678 filed May 30, 1989 abandoned.

BACKGROUND OF THE INVENTION

The present invention relates to a method and compositions for imaging the lymph nodes in a mammal, including a human.

The spread of cancer to regional or distant lymph nodes alters prognosis and treatment. Thus, proper determination of the stage of cancer in a patient requires evaluation of the lymph nodes along the lymphatic chain originating in the cancer. Imaging of lymph nodes is referred to herein as lymphography, and effective lymphography requires that the node be confidently identified, its size determined, and the intranodal anatomy or function be displayed. (The particular techniques disclosed herein may also appropriately be identified as "lymphadenography".) Imaging without direct infusion of contrast agent into the lymph system is referred to as indirect lymphography.

Cancer cells that lodge and grow in lymph nodes may be identified by node enlargement, by altered sieving function, or by altered phagocytosis. Normal lymph nodes range in size from 1–15 mm and can be enlarged by hypertrophy or hyperplasia. Size as a criterion for cancer evaluations is poor unless the nodes are very large and the patient is known to have cancer. Some imaging devices have adequate spatial resolution for sizing lymph nodes, but lack the tissue discrimination to confidently distinguish lymph nodes from other biological structures with similar shapes. These imaging modalities include x-ray, computed tomography, magnetic resonance imaging, and ultrasound. Radioisotope imaging does not have the required spatial resolution.

No contemporary imaging methodology can identify intranodal architecture without a contrast agent. A very few lymphatic channels in the body, usually those of the lower extremity, are large enough to isolate with a surgical procedure and these can be injected with a contrast agent that is carried to their lymph nodes.

Thus, today's conventional technology for imaging lymph nodes utilizes direct infusion of contrast agent into a lymphatic channel. In this procedure, known as lymphangiography, the radiologist directly cannulates a large lymphatic vessel and injects it with a contrast agent, generally an oily iodinated medium that opacifies the sinusoids of a lymph node draining the injected lymphatic vessel. Unfortunately, lymphangiography is only in limited use and does not provide satisfactory results in general. The process requires surgical exposure and identification of the lymph vessel. This is technically difficult, but is an established procedure for lymphatic vessels of the feet. The injection and procedure time is two to three hours and filming is routinely done 24 hours later. Further, the solutions injected tend to image only a few leg, pelvic, and abdominal nodes. It is uncommon to obtain images of any lymph nodes in the chest and neck area, despite the major importance of imaging these nodes in the evaluation and management of lung and breast cancers.

In lymphangiography, the contrast medium seems to be lodged in lymph node sinuses by creating a viscous obstruction that cannot be cleared by hydrostatic forces within the sinusoid. If the lymph node is totally obstructed by cancer cells to begin with or partial obstruction has created collateral channels, the abnormal node will not be visualized and the dye may eventually reach the bloodstream where it will embolize the lungs with adverse effects upon respiratory gas exchange. Some of the major shortcomings of lymphangiography include the fact that direct dissection is required, which is expensive, requires skill and limits repeatability; further, it carries some morbidity. Moreover, the majority of lymphatic drainage beds and their associated lymph nodes are inaccessible; among them are common targets of cancer such as the breast, the testis, the prostate, the cervix, the uterus, the kidneys, the liver, the intestines, and the lungs.

In addition to the danger associated with any prolonged procedure involving surgery, there are other dangers associated with lymphangiography that particularly relate to the contrast agent used in the procedure. If the agent chosen is water soluble or has a particle size that is too small, it will diffuse out of the lymphatic and may also pass through the lymph node too easily. Currently, x-ray lymphangiography utilizes an emulsified ethiodized oil for direct injection into the lymphatic system. This material has a large particle size, is highly viscous, has marginal toxicity, and embolizes the lymph node. In instances where there is an undetected, direct lymphatic-venous connection, ethiodized oils could be directed into the systemic circulation, with harmful and potentially fatal results.

Indirect lymphography with iodine formulations has usually been declared impossible (Mutzel, U.S. Pat. No. 4,367,216; Hoey, U.S. Pat. No. 4,225,725; Felder, et al., Swiss Patent 615,344) and iodine emulsions are also toxic (Mutzel). On the other hand, Japanese patent publication 42-25413 claimed development of an iodized vegetable fatty oil which was successful with intraperitoneal injection. No details are provided to substantiate the claim; no toxicity data are provided for indirect lymphography nor have there been any reports of other positive experiments since the application date of Sep. 28, 1965. Swiss Patent 615.344 discloses a crystal iodine formulation with a particle size of 1000– 5000 nm. They claim that the lymphatic vessels and lymph nodes below the sternum can be regularly visualized after intraperitoneal injection. This is dubious—both as to success and the specific nodes claimed from this injection route, particularly since there is no lymphatic flow downward from the sternum from the peritoneal cavity.

Other emulsions containing iodine have been proposed for lymphography, but have not been adopted for that purpose. See, e.g., Swiss patent No. 615,344 and Japanese published application No. 25413/67. Toxicity problems are one major concern. Also, particle sizes of 1000 nanometers and above are unsuitable for indirect lymphography (with the possible exception of intraperitoneal injection. The peritoneum offers a huge surface and facilitated absorption of most drugs. The lymphatic vessels of the peritoneum are more permeable, especially those of the diaphragm where uptake is facilitated by respiratory motion. Unfortunately, the lymph nodes accessible by this route are few and are of minimal clinical interest. Further, the intraperitoneal route places special limits on the toxicity of the lymphographic agent as direct access to the vascular space is facilitated by the thoracic duct.

Many researchers have experimented with radiolabeled materials as imaging agents for lymphography. There is a relatively rich literature on the development of radioactively tagged agents. Studies show lymphatic uptake and vascular exclusion is optimal for particles of about 40 nm. (See, e.g., Bergquist, et al. "Particle sizing and biokinetics of interstitial lymphoscintigraphic agents," Sem. Nucl. Med 13: 9–19, 1983.) These previous workers have also provided good information on animal models, pharmacokinetics and even human studies. (See also Ege, G.N., "Lymphoscintigraphy-techniques and applications in the management of breast carcinoma," Sem. Nucl. Med 13: 26–41, 1983). Unfortunately, radioactive isotopes trapped in lymph nodes provide poor spatial resolution and make it very difficult to determine details about the size of the nodes or the intranodal architecture.

$Au^{198}$ and $Ga^{67}$ have some avidity for lymph nodes and tumors, respectively. (See, e.g., Lymphatic Imaging: Lymphography, Computed Tomography and Scintigraphy, 2nd ed., M. Close and S. Wallis, eds., Williams and Wilkins Co., Baltimore, 1985). The former is too energetic for imaging and causes local tissue damage. The latter is interesting, but is only useful for intravenous use and is not suitable for staging of lymph nodes. Recently, protein-specific reagents have been suggested for treatment purposes. (See, e.g., Weinstein, et al., "Monoclonal antibodies in the lymphatics: toward the diagnosis and therapy of metastases," Science 218: 1334–1337, 1982).

At the moment, however, spatial resolution of isotope imaging devices precludes capitalizing on the selective distribution of tagged materials within lymph nodes.

In general, soluble and relatively small molecules such as albumin (<5 nM) are either better absorbed from the interstitial space into blood than into lymph or they are poorly retained by lymph nodes so that they are ineffective for imaging intranodal architecture.

We consider larger molecules to be particles and those up to 1 micron are called colloids while above 1 micron the particles are called suspensions. Microaggregated albumin fits in the former category while macroaggregated albumin is in the latter. Radiolabelled colloids have been of great interest for indirect lymphography, despite the low spatial resolution of current cameras. However, the methods for measuring the size of candidate agents are poor. Bergquist et al (Sem. Nucl. Med. 1983;13:9) list 9 different techniques for measuring radiocolloid particle size. None is totally satisfactory and many colloid preparations also have a wide range of particle sizes. A bimodal distribution in a particular preparation would invalidate a method that measures average size. Most preparations are better characterized by a complete distribution or histogram.

If the particles are rigid, then sizing is easier. But if the particles are deformable, then sizing is more difficult. Most techniques measure size in vitro, but size may increase or decrease in Vivo (Bergquist). Colloidal particles are usually coated with a stabilizer prior to administration and are also coated (opsonized) in vivo. The effective particle size includes the coat as well as the core, so this complicates the measurement. For imaging uses, the active contrast agent is usually limited to the core material.

The particles enter the lymphatics from the interstitium through gaps between lymphatic endothelial cells or by transcellular endo-exocytosis. The gaps change in calibre with physiologic or pathologic conditions. Entry of the particle into the gap is believed to be a hit-or-miss affair and should be weakly related to particle size at dimensions less than the size of the gap. On average, smaller particles (10–50 nM) are more likely to enter than larger particles. However, larger particles usually carry more imageable material and are more effective per particle in altering the image intensity. Thus, predicting imaging efficacy for a particular formulation is complicated. As particles approach 1000 nM, their uptake into lymphatics is so poor that they become ineffective. Very large particles in the interstitial space must be carried away by phagocytes or reduced in size by local processes.

Once particles reach the lymphatic space, a functional lymph node can very efficiently remove them, even if they are as large as a few thousand nanometers. This process requires particle coating, adhesion, and phagocytosis. Cancer deposits in the lymph node destroy lymph node sinusoids and cancer cells have little or no phagocytic capacity. For both these reasons, cancerous regions accumulate particles poorly.

Virtually all particles—and the list is long and varied—selectively target normal parts of the node from the lymph in which they are carried. The influence of "sick phagocytes" upon sequestering particles in lymph nodes is unknown, but most processes causing hyperplasia or hypertrophy create functioning phagocytes and these nodes, though large, accumulate particles.

Ethiodol—the standard lymphangiographic agent—is poorly phagocytosed and acts by sinusoidal blockade. This accounts for its spotty distribution creating a grainy appearance in normal nodes at moderate magnification. The germinal follicles in lymph nodes have few sinusoids and also few functioning macrophages. Both Ethiodol and particles will be sparsely accumulated in these regions.

A lymph node totally replaced by other cells, usually cancer, will receive no lymph but does continue to receive blood. Neither direct nor indirect lymphography will be effective in defining intranodal architecture in this circumstance. It may still be possible to target such nodes with intravascular agents.

Clearly, despite the elegant compartmental models of Strand et al. (J. Nucl. Med. 1979;20:1038), most attempts to evaluate indirect lymphography agents rely heavily on actual animal experimentation. Mikheev (Atomic Energy Review 1976;14:1) writes, "As the measurement of colloid particle size presents great difficulties and the behavior of colloidal solutions in the body is only indirectly related to particle size, it is more useful to control colloidal solutions by biological studies in laboratory animals." On the other hand, it would be much easier to screen proposed agents in vitro were size distribution and imaging efficacy methods available and accurate. Such data would dramatically reduce the burden for animal studies and would enable the investigator to identify anomalous responses that might aid in further understanding of this complex biological process.

There is at least one reported attempt at indirect lymphography through injection of radiopaque perfluorocarbons subcutaneously into the peritoneal or pleural spaces or into the lung parenchyma. However, animal tests involving injection of both neat and emulsified radiopaque perfluorocarbon failed to produce clinically useful information. D. Long, et al., Radiology 133: 71–76 (1979). Instead, radiopacification of lymph nodes with emulsions was sporadic and was observed only in one animal eight months following administration of the perfluorocarbon. This outcome is too inconstant and too delayed for clinical applications.

Other attempts to perform direct or indirect lymphography have utilized dimers of iodinated water soluble agents. The dimer increases molecular size, and reduces diffusion from the lymphatic to some degree; however, these small soluble agents appear to provide only transient opacification of the lymph node.

Accordingly, there is a need for a lymphographic technique and contrast agent that permits imaging of lymph nodes in any desired area of the body within a reasonable time period. Such imaging would identify location, size, and internal architecture of regional lymph nodes of interest and would permit differentiation between lymph node enlargement due to hypertrophy and hyperplasia of normal node constituents, on the one hand, and neoplasia, on the other hand.

Moreover, there is a need for a lymphographic procedure that minimizes procedure time and patient discomfort, while reducing the dangers of the procedure.

These and other objectives are met by the present invention.

SUMMARY OF THE INVENTION

The present invention utilizes contrast agents that have particular characteristics that facilitate their uptake into lymphatics and retention in the regional lymph nodes. Although a wide variety of contrast agents can be used, we have discovered that they must have one common parameter: appropriate particle size.

Lymph nodes process material delivered by the afferent lymphatics; the material delivered is fluid, particulates, and cells. The lymph node removes material by sieving or phagocytosis. Noncellular material enters the lymphatics from the interstitial fluid through gaps between the lymphatic endothelial cells, and also by endocytosis. Because the gaps are not fixed in an anatomic sense, any given gap can intermittently open and close. The buildup of interstitial fluid or tissue motion tends to open the gaps wider or more frequently, increasing the amount and size of material that enters.

Fluids and particles up to 5 nm in diameter within the interstitial space are not preferentially taken up by the lymphatic system, but are instead absorbed more rapidly by the blood circulation. On the other hand, particles larger than 5 nm are poorly absorbed by blood capillaries. When the particle size reaches 900 nm, 1000 nm, and greater, particles are expected to only poorly penetrate into the lymphatic system. Particles between 5 or 10 nm and 500 or 900 nm, then, are those we have identified as most likely to be preferentially taken up by the lymphatic system and to be retained in the lymph nodes.

In brief, then, the present invention is directed to contrast agents suitable for imaging by one or more imaging techniques, which agents are in particulate form and are adapted to be preferentially taken up by the lymphatic system upon percutaneous administration. These contrast agents can be radiopaque materials, MRI imaging agents, ultrasound imaging agents, and any other contrast agent suitable for a device that images an animal body. They are preferably nontoxic, and should have a particle size between about 5 or 10 nm, as a minimum, and about 500 or 900 nm, as a maximum. Of course, in any given particulate system, particle sizes usually form a distribution. Thus, it is preferred that the mean particle sizes fall within the range of 5 to 900 nm, preferably within the range of 10 to 500 or 800 nm. Alternatively, it is desired that at least 80 percent of the particles, by volume, fall into the range of about 5 or 10 nm to about 800 or 900 nm. In preferred embodiments, the average or mean particle size is at least 20 nm and may also advantageously be less than about 500 nm. Formulations in which the mean particle size is no more than 300 or even 250 nm are also contemplated. Also, we believe there are particular advantages to formulations in which at least 20% of the particles, by volume, are less than 300 nm or 200 nm.

The particular type of particle can be selected from a wide range of possibilities. Polymers of appropriate size can be used. Colloids are also within the scope of the present invention, as are emulsions with appropriate particle size.

In one embodiment of the present invention, the mean size of the particles in the emulsion is less than about 250 nm. The emulsion droplet is preferably stabilized with an emulsification agent, such as a surfactant. Particularly advantageous are phospholipid surfactants, which inherently may affect the biocompatibility, uptake by the lymphatics, and overall rheological properties. The appropriate size may also be obtained with small liposomes that carry contrast media. Finally, the viscosity of the formulation is believed to be significant. Our data suggest that large particle sizes and viscous compositions do not readily and rapidly enter the lymphatic system. Thus, we prefer compositions having a viscosity measured at 25° C. at a shear rate of 11.5 $sec^{-1}$ of 50 cps or less, preferably not more than 35 or 40 cps, and most preferably less than about 20 or 25 cps. We have had good results with emulsions having viscosities of under 10 cps and particularly under about 5 cps.

For x-ray and computed tomography imaging, the contrast agent should have an adequate electron density to render it visible with these techniques. Suitable electron density is achieved, e.g., in compounds with bromine or iodine moieties, and in materials comprising or including radiopaque metal atoms.

For MRI, one looks to materials that have adequate nuclear or relaxation properties for imaging that are different from the corresponding properties of the tissue being imaged. Either an imageable nucleus (such as $^{19}F$) or a ferromagnetic or paramagnetic material can be used with appropriate MRI equipment.

Ultrasound and x-ray imaging, including the use of digital subtraction techniques, may also be utilized according to another embodiment of the present invention. Ultrasound contrast agents can be selected on the basis of density or acoustical properties.

The present invention also suggests methods for preparing emulsions, and further suggests methods for concentrating such emulsions, including dialysis, ultrafiltration, and reverse osmosis.

Preferred contrast agents include emulsions of perfluorooctylbromide ("PFOB") and other radiopaque perfluorocarbons, imageable fluorocarbon compounds, perfluoroalkylated ethers and perfluoroalkylated ether bromides, as well as colloids or particles of gold, iron, chromium, gadolinium, yttrium, zirconium, hafnium, tin or antimony as oxides, phosphates, sulfides, or silicates. Paramagnetic, superparamagnetic, and ferromagnetic particles of chromium, gadolinium, iron, manganese, ferrites, and magnetite are also contemplated, as are imageable compounds linked to or incorporated with dextran, albumin, latex, polystyrene, or other particulate materials of appropriate size.

Other compounds are also contemplated by the present invention, including magnetic polymer particles, organomagnetic particles, microspheres, and biologically active magnetic particles such as those discussed in U.S. Pat. No. 4,795,698 to Owen, and in the patent references cited therein. The particles, colloids, or emulsions may have stabilizers to assure size and dispersion in vivo. Moreover, the particles may be coated with various materials, such as the polysaccharide-coated iron oxide particles suggested in U.S. Pat. No. 4,452,773 to Molday.

The present invention further contemplates the use of hydrophobic particles, insoluble metal colloids, lipid-soluble iodinated compounds, or other iodinated compounds, including those in which the iodine atom is contained within the perfluorocarbon molecule. In one particularly preferred embodiment of the invention, however, the particulate is noniodinated. Although some embodiments of the invention may utilize iodinated fluorocarbons, it is preferred that non-fluorocarbon iodine compounds, such as iodinated oils and crystals, are excluded.

The method of the present invention involves interstitial injection (or other interstitial administration) of the contrast agent in the vicinity of the lymph nodes to be imaged. Interstitial injection includes injection subcutaneously (under or in the skin) and intraparenchymal injection (into an organ), but does not include injection into a body cavity, such as intraperitoneal injection. In the case of cancer patients, the involvement of lymph nodes is preferably evaluated by injecting the contrast agent in proximity to the cancer. The contrast material is then taken up by the lymphatic system, and tends to localize in lymph nodes afferent to the uptake site. Thus, the contrast agent follows the same route as a metastatic tumor cell would be likely to follow within the lymphatic system.

After an appropriate waiting period, usually a few hours to a few days, the lymph nodes are imaged and the size and intranodal anatomy of the nodes are evaluated in order to determine their location and normality, including possible cancerous involvement. A waiting period of between 3 days and one month is preferred, and between 4 days and 15 days is particularly preferred.

DETAILED DESCRIPTION OF THE INVENTION

There are a number of particulate contrast materials that can be used in the practice of the present invention.

1. Fluorocarbon Emulsion Contrast Agents

One particularly preferred category of contrast materials includes radiopaque fluorocarbons in the form of emulsions. These materials are substantially nontoxic, and can be eliminated quite readily from the body. We have prepared perfluorooctylbromide ("PFOB") emulsions with a range of particle sizes to be injected subcutaneously for imaging lymph nodes. Through a series of experiments it was determined that a particle size range of about 10 to 900 nanometers (nm) was particularly suitable. Emulsions with these properties were prepared with PFOB and egg yolk phospholipid in an aqueous vehicle. (Of course, other concentrations may also be used.) Emulsification was accomplished as reported in Published European Applications Nos. 231,070 and 307,087, and U.S. Pat. No. 4,865,836.

These emulsions are often more dilute than those used for liver-spleen imaging but also have much smaller target tissue mass. The viscosity of the emulsion is preferably less than about 50 cps at 25° C. measured at a shear rate of 11.5 sec$^{-1}$. If necessary, the volume of the emulsion used may be decreased by concentrating the emulsion via physical methods, such as centrifugation. Concentration of the emulsion may also be achieved using reverse osmosis, dialysis, or other methods, including ultrafiltration, microfiltration, and ultracentrifugation. In addition to PFOB, other radiopaque fluorocarbons can be utilized, such as nontoxic fluorocarbon iodides, and the perfluorocarbon bromides disclosed, for example, in U.S. Pat. Nos. 3,818,229, 3,975,512, and 4,073,879. The fluorocarbon iodides may be mono-, di-, or tri-iodinated perfluorocarbons. In the fluorocarbon embodiments of the present invention, the fluorocarbon is preferably in the form of an emulsion, with a mean particle size of from about 5 to 900 nm, and preferably less than about 500 nm. Most preferably, a mean particle size of less than about 300 nm is utilized.

The present invention includes radiopaque fluorocarbon emulsions suitable for percutaneous lymphography, comprising an aqueous phase and a fluorocarbon phase, wherein the fluorocarbon phase comprises particles having a mean particle size as set forth above. PFOB emulsions are preferred. Moreover, the most preferred fluorocarbon emulsions are highly concentrated, and have a fluorocarbon concentration of at least about 30%, preferably 35% or 40%, and more preferably at least about 50% or 55% fluorocarbon, w/v. At the upper end, the emulsions preferably have no more than about 125% fluorocarbon, w/v. While emulsions can be prepared in any suitable way, the preferred method involved passing a mixture of water, fluorocarbon, surfactant, and any desired excipients through a high pressure mechanical emulsifying apparatus, in which the mixture is subjected to high shear conditions or conditions of high mechanical stress. Such emulsifiers typically operate at pressures of 2000 psi to 25,000 psi and direct the mixture at high speed along a nonlinear path to generate the emulsion. Usually several passes through the apparatus can be used to generate a uniform and stable emulsion. Suitable emulsification devices are commercially available from Microfluidics Corporation (Newton, Mass.), model number M-110. Also appropriate for use is the Ramnie Homogenizer 12-51 from Albertslund (Copenhagen, Denmark), as well as other high pressure valve homogenizers.

In order to control the particle size and rheological properties, we have found that the initial concentration of fluorocarbon phase is important. Optimal properties seem to be generated with fluorocarbon concentrations between 20% and 0%, w/v, and 30% emulsions have provided good results in our studies, forming emulsions with mean particle sizes at or below about 500 nm and viscosity less than 50 cps at a shear rate of 11.5 sec$^{-1}$ measured at 25° C.

After formation of the emulsion, it is advantageous to sterilize it in a steam autoclave. Suitable sterilization parameters include sterilization at about 110° C. for about 15 minutes. Either before or after sterilization, the emulsion can be concentrated in order to minimize the volume of material administered to the patient.

Concentration can be accomplished by dialysis, ultrafiltration, reverse osmosis, and the like. In particular, DDS microfiltration (nanofiltration) membrane GRM1.0PP (Niro Atomizer Food & Dairy Inc., Hudson, Wis.), comprised of polysulphone and having a molecular weight cutoff of 1 micron ($\mu$)—1$\mu$ being equivalent to a molecular weight of 10 million—may be utilized; also effective is DDS microfiltration membrane GRM0.2PP, with a molecular weight cutoff of 0.2$\mu$, or GRM0.1PP, with a molecular weight cutoff of 0.1$\mu$. Alternatively, if ultrafiltration is used, the membrane which is most effective is DDS polysulphone ultrafiltration membrane CR10PP, with a molecular weight cutoff of 500,000 (0.05$\mu$). All of the aforementioned membranes are usable at temperatures ranging from 0° C. to 75° C. and at pH ranging from 1–13. If ultrafiltration is the process of choice, approximately $\leq$100 pounds per square inch (psi) is appropriate. If nanofiltration is utilized, 100–400 psi may be used, whereas approximately 600 psi is appropriate for reverse osmosis.

2. Other Radiopaque Contrast Agents

In addition to radiopaque fluorocarbon emulsions, other radiopaque materials can be used in the practice of the present invention, so long as they are in the form of injectable materials having the required particle size characteristics, appropriate fluidity, and adequate safety.

Iodinated materials have long been used as contrast agents in computed tomography and x-ray procedures. There are a number of water-insoluble organic compounds, for example, that have been iodinated in the prior art. Ethiodated oils, for example, are presently used in lymphangiography. U.S. Pat. No. 4,404,182 discloses ethiodized oil-based contrast agents, including emulsions thereof. Although the emulsions in that patent had particle sizes of 2–3 microns, emulsification techniques similar to those described above can be used to form emulsions with suitably small particle sizes for use in the present invention.

Iodinated fatty acid esters of poppyseed oil and other oils are currently in use for lymphangiography. These materials can be used in the practice of the present invention when formulated into emulsions having the requisite particle size. Moreover, other iodinated fatty materials or corresponding brominated materials can similarly be used in practice of the present invention. Some toxicity has been reported for these materials; accordingly, less toxic agents are preferred. However, use of these already-approved materials in the practice of percutaneous lymphography is contemplated as within the scope of the present invention.

In addition to iodinated or brominated materials, a number of other electron-dense materials can be used in the present invention. The electron density can be provided by non-radioactive elements or compounds such as gold or iron, chromium, gadolinium, yttrium, zirconium, hafnium, tin or antimony as oxides, phosphates, sulfides, or silicates, as well as other nonradioactive metals. The foregoing can advantageously be utilized in the form of colloids or particles of appropriate size.

Alternatively, other agents may be used to form particles having the requisite size from the foregoing materials. It is well known that dextran, albumin, latex, polystyrene, and other proteins, synthetic polymers, and the like can be obtained in particles having the size characteristics set forth above. Liposomes can also be formed using conventional techniques that have the necessary particle sizes. While these particles perse are generally unsuitable for imaging use, they can be used in the present invention in combination with imageable materials. Thus, for example, submicron particles of radiodense materials can be linked to, encapsulated by, or physically incorporated into these particulate compounds using known methods. Before use, they are preferably suspended in a suitable injectable carrier, such as phosphate buffered saline, optionally in combination with of any of the well-known physiologically acceptable surfactants. Preservatives and antimicrobials may also be used in conventional concentrations.

3. MRI Imaging Agents

While the foregoing radiodense materials can be used for computed tomography and x-ray imaging of the lymphatic system, MRI contrast agents are also desirable in the practice of the present invention. MRI has some technical advantages over conventional radiology and radiolabeling in that lymph nodes have inherent differences in their proton spin relaxation compared to that of fatty tissue; however, there is little tissue contrast within nodes, and thus node enlargement is the only available criterion of abnormality, when MRI is used.

The terms "T1" and "T2" are terms of art that refer generally to the relaxation time of proton spins. The proton spin density and relaxation times are essentially what proton MRI detects. Since fatty tissue has short T1 and long T2 relative to other tissues, the superparamagnetic or ferromagnetic class of agents that selectively shorten T2 is favored. A superparamagnetic particle of optimum size may be administered subcutaneously or intraparenchymally to contrast any desired chain of lymph nodes. One may also coat such particles with monoclonal antibody to provide a degree of cell specificity within the lymph node or other tissue of interest. A dextran coating may also be used to reduce aggregation.

Although inherent tissue contrast is a major strength of MRI, some tissue pairs lack inherent contrast and both tissue specificity and functional characterization are suboptimum. Contrast agents thus have the potential to improve MRI for some clinical applications. In particular, they can be used to advantage in imaging of the lymphatic system in accordance with the present invention.

There are two major classes of contrast agents: paramagnetic and superparamagnetic. Paramagnetic agents have unpaired electron spins that facilitate relaxation of nuclei, usually water protons, that can closely approach them (within 1 nm). These agents decrease both T1 and T2, are effective in μM concentrations, and can be incorporated in chelates with favorable biodistribution and toxicity profiles. Schering's patented product, GdDTPA (gadolinium diethylenetriaminepentaacetic acid), is an outstanding example of several commercially available such agents. To be useful for lymphography, this class of agents must be incorporated into macromolecules to avoid uptake by the systemic circulation. Combination with albumin, other biological molecules of appropriate size, latex, dextran, polystyrene or other non-toxic natural or synthetic polymer, or encapsulation in liposomes, can be accomplished as set forth above.

Although this represents one substantial aspect of the present invention, there are at least two reasons for preferring the superparamagnetic or ferromagnetic class. First, for detecting the size of lymph nodes, the fat surrounding the node provides a valuable contrast to the node itself. The presence of paramagnetics in a lymph node would principally reduce T1 and would make lymph nodes more isointense with surrounding fat, and thus more difficult to identify. This could be overcome with subtraction techniques, but lymph node uptake from interstitial depots occurs over 2–72 hours and this makes precise repositioning (for subtraction) of structures measuring less than 2 cm somewhat difficult. Second, clusters of unpaired spins that create superparamagnetic or ferromagnetic fields within the magnet are much more potent and selectively decrease T2. As lymph nodes already have shorter T2 than fat, a superparamagnetic agent would increase tissue contrast against fat.

Of equal importance is the fact that the physical size of agents that are required for lymph node targeting is virtually in the same size domain as many suitable superparamagnetic agents. This is true of particles of superparamagnetic ferrites and magnetites. Finally, the superparamagnetics are effective at all fields and with nearly all pulsing sequences, thus facilitating their ultimate use in clinical circumstances.

Happily, many of the contrast agents discussed herein can be used in multimodal imaging. For example, the MRI contrast agents are usually also electron dense materials, and thus can be used for both CT or x-ray imaging as well as MRI. PFOB emulsions are also quite useful for MRI. Moreover, many of the foregoing materials, such as fluorocarbon emulsions, magnetite suspensions, and the like can be used as ultrasound contrast materials as well.

Among potential imaging agents, our data indicate that the following contrast agents, among others, would be effective:

1. For CT and Digital x-ray: PFOB emulsions; emulsions of ethiodized oils or other iodinated or halogenated lipophilic materials;
2. For ultrasound: PFOB emulsion, magnetite suspensions, other heavy or air trapping products.
3. For MRI: PFOB emulsion, metal dioxide colloids such as zirconium dioxide colloid or $Gd_2O_3$ colloid, paramagnetic macromolecules, supermagnetic or ferromagnetic particles, other similar emulsions, and small liposomes with entrapped materials.

4. Method for Performing Percutaneous Lymphography

The methods of the present invention are straightforward. In brief, an imageable amount of a suitable contrast agent prepared as set forth above or in the Examples that follow is injected interstitially (subcutaneously or intraparenchymally) into the animal to be imaged. After sufficient time has elapsed to permit localization of the agent into the lymphatic system of the animal, a conventional imaging step is performed.

Because of the preferential uptake of the contrast agent into the lymphatic system, relatively small amounts of contrast agent are needed. For example, to image the lymph nodes of the neck in a human using CT and ultrasound, approximately 1–5 cc of 30% w/v PFOB emulsion is injected subcutaneously in the vicinity of the lymphatic tributaries draining to the target node, preferably in front of or behind the ear, or at the site of a known tumor. Similarly, approximately 1–2 cc of $Gd_2O_3$ microcolloid suspended in phosphate buffered saline at a concentration of 0.1–0.5M can be used for MR imaging of the same area. In both cases, the amount of time between injection and imaging is between about ½ hour and 72 hours, preferably between about 24 and about 48 hours.

Similarly detectable amounts of other contrast agents will be readily determinable to those of skill in the art by reference to the foregoing information. Moreover, a simple dilutional and time study in rabbits of the type reported in the Examples can be used to readily determine suitable amounts for other contrast agents and/or imaging methodologies.

The present invention is particularly suitable for imaging lymph nodes for detection of neoplasms or other disease. We have found that there is some variability in the uptake of these materials by region. In the rabbit, for example, greatest uptake is from forelimb to axillary node, followed in order by: hindlimb to popliteal node, cheek to cervical node, chest to axillary node, and thigh to inguinal node.

In humans, then, injection into the hand or arm is used to image the axillary nodes, injection into the foot or leg is used to image the popliteal node, injection into the cheek or face is used to image the cervical node, injection into the chest is used to image the axillary node, and injection into the thigh is used to image the inguinal node.

5. Preparation of Medicaments for Percutaneous Lymphography

The present invention also includes the use of the particulate materials described herein in the preparation of a medicament for use in performing indirect or percutaneous lymphography on the human or other mammalian body. The medicament may be prepared, for example, by suspending the imaging particles in a pharmaceutically acceptable injectable carrier of conventional composition. The carrier, in the case of an emulsion, is the aqueous phase of the emulsion. Suitable osmotic and buffering agents may be used in the formulation, as is conventional in the pharmaceutical arts. The medicament is preferably packaged with directions or instructions indicating that it is to be used for indirect lymphography by interstitial administration, and imaged within one month or less. Also, the medicament may be packaged in a container accompanied with an indication that the formulation has received governmental regulatory approval for use in humans for indirect lymphography. Such approval, for example, is obtained from the U.S. Food and Drug Administration for medicaments solid in the United States.

Particular embodiments of the present invention can be readily understood by reference to the following Examples, which are intended to be representative and not limiting.

EXAMPLE I

Preparation and Concentration of Perfluorocarbon Emulsion

An emulsion having suitable particle size and rheological properties was prepared by forming a mixture comprising:

| Ingredient | Percent (w/v) |
| --- | --- |
| Perfluorooctylbromide | 30 |
| Egg yolk phospholipid | 6 |
| Mannitol, USP | 0.4 |
| Sodium chloride | 0.5 |
| Disodium calcium edetate | 0.15 |
| d-α-tocopherol acetate | 0.05 |
| Buffered at pH 8.2 prior to sterilization | |

This mixture was passed 5 times through a high pressure mechanical emulsifier (Model M-110, Microfluidics Corporation, Newton, Mass.) at a pressure of 15,000 psi. The resulting emulsion was terminally sterilized at 121° C. for 15 minutes. The sterilized emulsion had a median particle size diameter of 190 nm with 53% of the PFOB particles less than 200 nm and 3.4% of the PFOB particles greater than 500 nm. The viscosity of this preparation at 25° C. was 3.4 cps at a shear rate of 11.5 $sec^{-1}$ and 3.0 cps at a shear rate of 46 $sec^{-1}$.

Using the same formulation, the particle size distribution was modified by varying the number of passes through the emulsification apparatus, to give the following emulsions A–D:

| Batch | Mean Diameter nm | Volume Fraction, % | |
| --- | --- | --- | --- |
| | | <200 nm | >500 nm |
| 1 | 200 ± 90 | 61.4 | 2.0 |
| 2 | 210 ± 100 | 54.6 | 2.0 |
| 3 | 180 ± 80 | 73.0 | 0.5 |
| 4 | 310 ± 210 | 40.0 | 36.0 |

These emulsions were used in generating the data in Example III, below.

The emulsions of this example can be concentrated, if desired, to form higher concentration emulsions. Concentration is accomplished via utilizing dialysis, ultrafiltration, nanofiltration, reverse osmosis, and the like. For example, one embodiment uses DDS microfiltration (nanofiltration) membrane GRM1.OPP (Niro Atomizer Food & Dairy Inc., Hudson, Wis.), comprised of polysulphone and having a molecular weight cutoff of 1 micron (μ), although DDS microfiltration membrane GRM0.2PP, with a molecular weight cutoff of 0.2μ, or GRMO.1PP, with a molecular weight cutoff of 0.1μ, may also be used effectively. Another preferred embodiment employs ultrafiltration as the concentrating method. The membrane which is most effective in such applications is DDS polysulphone ultrafiltration membrane CR1OPP, with a molecular weight cutoff of 500,000 (0.05μ). All of the aforementioned membranes are usable at temperatures ranging from 0° C. to 75° C. and at pH ranging from 1–13. If ultrafiltration is the process of choice, approximately ≦100 pounds per square inch (psi) is appropriate. If nanofiltration is utilized, 100–400 psi may be used, whereas approximately 600 psi is appropriate for reverse osmosis.

Alternatively, a higher concentration emulsion can be prepared ab initio using the procedure of this Example while increasing the PFOB concentration. Decreases in phospholipid emulsifier may be desirable at higher concentrations of PFOB (e.g., 4.5% phospholipid for a 75% PFOB emulsion).

EXAMPLE II

Preparation of MRI Contrast Agents

Magnetite spheres were obtained as Biomag M4125 from Advanced Magnetics, Inc. (Boston, Mass.) having a mean particle size of 500 nm. (Another commercial source for magnetite particles is Immunicon (Huntington Valley, Pa.).) Alternatively, particulates are prepared via the procedures described in Elmore, W. C., Phys. Rev. 54: 309–310 (1939) or McNab, et al., J. Appl. Physics 39: 5703–5711 (1968), which are incorporated herein by reference. These particles are studied uncoated. In addition, we prepared particles coated with dextran and particles coated with serum albumin to reduce aggregation and to facilitate lymphatic uptake. Coated particles are prepared generally as set forth by Molday, et al., J. Immunol. Meth. 52: 353–367 (1982).

GdDTPA was coupled to 60,000 mw dextran using the bis anhydride of DTPA via the procedures described in Hnatowich and Siegel, Science 220: 613–615 (1983).

EXAMPLE III

Percutaneous Lymphography of the Rabbit with PFOB

A. Protocol 1

Adult male NZW rabbits each weighing approximately 2–2.5 kg were given subcutaneous PFOB emulsion at various time intervals using a 30% w/v PFOB emulsion of Example 1 (first formulation) and a 0.6 gm/injection site dose. The following table represents the mean and standard deviation values of PFOB concentration (mg PFOB/gm tissue) at these various time intervals:

| Time Interval | Lymph Node | Mean | Std. Dev. | No. Samples |
|---|---|---|---|---|
| 24 hrs | Cervical[1] | 9.20 | 4.74 | 11 |
| | Axillary[2] | 27.35 | 12.57 | 11 |
| | Inguinal[3] | 6.20 | 6.63 | 11 |
| | Popliteal[4] | 16.57 | 4.51 | 11 |
| 48 hrs | Cervical | 17.72 | 10.46 | 3 |
| | Axillary | 39.46 | 27.16 | 3 |
| | Inguinal | 6.09 | 6.47 | 3 |
| | Popliteal | 27.73 | 9.35 | 3 |
| 72 hrs | Cervical | 18.69 | 14.73 | 9 |
| | Axillary | 75.34 | 23.39 | 9 |
| | Inguinal | 6.82 | 9.19 | 9 |
| | Popliteal | 39.09 | 14.89 | 9 |
| 1 week | Cervical | 19.90 | 14.51 | 12 |
| | Axillary | 86.78 | 37.68 | 12 |
| | Inguinal | 3.59 | 4.77 | 11 |
| | Popliteal | 47.28 | 19.60 | 12 |
| 2 weeks | Cervical | 9.34 | 7.74 | 6 |
| | Axillary | 55.39 | 19.88 | 6 |
| | Inguinal | 5.03 | 5.24 | 5 |
| | Popliteal | 27.32 | 10.82 | 6 |
| 1 month | Cervical | 11.82 | 5.53 | 8 |
| | Axillary | 46.86 | 6.79 | 8 |
| | Inguinal | 0.64 | 0.27 | 4 |
| | Popliteal | 20.85 | 3.42 | 8 |

[1]Injection site: cheek
[2]Injection site: forepaw
[3]Injection site: thigh
[4]Injection site: hindpaw

B. Protocol 2

To demonstrate the efficacy of indirect lymphography using PFOB, four separate 30% emulsions were prepared and administered to rabbits at a dose of 0.3 gm into each forepaw. (These are emulsions A–D in Example 1.) Each rabbit was imaged by CT using thin section, contiguous slice techniques to identify and quantitate radiopacity of the axillary node. Two different methods of measuring node intensity showed excellent correlation (CT console expressed in Hounsfield units, Optimas software on a Zenith workstation expressed in arbitrary units, R=0.99).

Each rabbit was imaged only once and then sacrificed. Axillary nodes were removed and PFOB concentration determined by Gas Chromatography. The correlation between peak CT intensity of enhanced node and lymph node PFOB content was significant (R=0.82 for Hounsfield units, R=0.79 for Optimas units). The imaging intervals after forepaw injection were days (n=20); 7 days (n+12); 10 days (n=7); and 12 days (n=13). At all four time periods, each 30% emulsion showed consistent and dense opacification of the target node. Peak opacification was seen at 10 days, but all time periods were judged to identify normal intranodal architecture with sufficient enhancement for clinical diagnosis. Blood chemistry, histology of lymph nodes and injection sites, and clinical follow-up of the rabbits for weeks and monkeys for months revealed no evidence of local or systemic toxicity.

All of these emulsions demonstrated efficacy in indirect lymphography.

C. Protocol 3

Percutaneous lymphography with 30% PFOB emulsion was performed in six (6) Macaques weighing 6–25 lbs. each. 1.0 cc of the emulsion was injected into the toe web spaces of the left foot. After 3, 7, and 17 days, the left inguinal node was easily visualized on thin-slice CT images in all six primates. These animals were followed clinically for more than 1 year without any untoward effects evident at the injection site or in their general health.

EXAMPLE VI

To demonstrate the poor results of lymph node opacification with larger particles, a colloidal suspension of 0.2 $Gd_2O_3$ with an average particle size of 932 nM was injected subcutaneously in cheek and sternum of rabbits. These rabbits were serially imaged over 30–60 days. The injection sites were densely opacified on CT scans but no lymph node opacification was obtained in any rabbit. Dilution and coating of the radiopaque colloidal particles with dextran (two additional injections) did not lead to detectable absorption from the injection site or lymph node opacification.

EXAMPLE V

MR Imaging with Gadolinium Contrast Agent

GdDTPA coupled to 60,000 mw dextran (from Example II) was administered subcutaneously to twenty rats along with India ink to visually mark the lymph nodes. The rats were sacrificed twenty-four hours later and their lymph nodes showed the characteristic high field peak of Gd-macromolecules. Rat lymph nodes are too small to image with our Signal systems.

EXAMPLE V

MR Imaging with Superparamagnetic Magnetite Particles

Magnetite disproportionately decreases T2 relaxation of adjacent protons. Initially, ether-anesthetized rats received 0.1 ml (1 mg iron) of magnetite spheres (from Example II) in each foot pad. 12–16 rats in each group were sacrificed and their lymph nodes were examined with in vitro relaxation time measurements. The T2 of their lymph nodes were as follows:

|  | Control | 3 hrs | 6 hrs | 12 hrs | 24 hrs |
|---|---|---|---|---|---|
| T2 (mean) | 65 | 61 | 58 | 39 | 29 |

The relatively slow uptake suggested that the particles could be clumping and/or that inactivity following the anesthesia was delaying lymphatic absorption. For this reason, 1% dextran was added to reduce aggregation and other rats were exercised for 15 minutes by forced swimming and sacrificed three hours later. The results are shown below.

|  | Magnetite without dextran | Magnetite without + swim | Magnetite with dextran | Magnetite + dextran + swim |
|---|---|---|---|---|
| T2 (mean) | 48 | 43 | 33 | 22 |

Although the invention has been described in the context of particular embodiments, it is intended that the scope of coverage of the patent not be limited to those particular embodiments, but be determined by reference to the following claims.

I claim:

1. A method for diagnosing disease affecting the lymph nodes through indirect lymphography using ultrasound or magnetic resonance imaging, comprising the steps of:

interstitially administering a diagnostically effective, non-toxic amount of a non-radioactive contrast agent to a mammal, wherein said agent is in particulate or colloidal form, said agent having a mean particle size from about 5 to about 900 nanometers in diameter and being imageable with sufficient resolution through ultrasound or magnetic resonance imaging to permit visualization of intranodal architecture;

permitting the contrast agent to localize in the lymph nodes; and imaging the lymph nodes of the mammal in which said contrast agent has localized with magnetic resonance imaging or ultrasound within about 1 month of said administration.

2. A method according to claim 1, wherein at least 80% (by volume) of said particles are between about 10 and about 500 nanometers in diameter.

3. A method according to claim 1, wherein the mean particle size is between about 10 and about 500 nanometers.

4. A method according to claim 1, wherein said particles belong to the superparamagnetic or ferromagnetic class of agents.

5. A method according to claim 1, wherein said particles comprise insoluble metal colloids.

6. A method according to claim 1, wherein said imaging is performed by MRI.

7. A method according to claim 1, wherein said imaging is performed by ultrasound.

8. A method according to claim 1, wherein said administration comprises subcutaneously injecting a hand, foot, or limb to image axillary, popliteal, or lingual nodes.

9. A method according to claim 1, wherein said administration comprises subcutaneously injecting the chest or face to image the axillary or cervical nodes.

\* \* \* \* \*

UNITED STATES PATENT AND TRADEMARK OFFICE
CERTIFICATE OF CORRECTION

PATENT NO. : 5,496,536
DATED : March 5, 1996
INVENTOR(S) : Gerald Wolf

It is certified that error appears in the above-indentified patent and that said Letters Patent is hereby corrected as shown below:

Column 3, Line 54, change "in Vivo" to --in vivo--.

Column 6, Line 21, change "25°C. at" to --25°C at--.

Column 7, Line 60, change "at 25°C. measured" to --25°C measured--.

Column 8, Line 38, change "20% and 0%" to --20% and 40%--.

Column 8, Line 45, change "110°C. for" to --110°C for--.

Column 8, Line 52, change "Hudson, Wis" to --Hudson, WI--.

Column 8, Line 62, change "0°C. to 75°C. and" to --0°C to 75°C and--.

Column 8, Line 64, change "≤ 100" to --≤ 100--.

Column 9, Line 46, change "particles perse" to --particles per se--.

Column 12, Line 45, change "121°C. for" to --121°C for--.

Column 12, Line 49, change "25°C. was" to --25°C was--.

Column 13, Line 7, change "Hudson, Wis)" to --Hudson, WI)--.

Column 13, Line 10, change "GRM0.1PP" to --GRM0.1PP--.

Column 13, Line 16, change "0°C. to 75°C. and" to --0°C to 75°C and--

Column 13, Line 19, change "≤ 100" to --≤ 100--.

Column 13, Line 32, change "(Boston, Mass.)" to --(Boston, MA)--.

UNITED STATES PATENT AND TRADEMARK OFFICE
CERTIFICATE OF CORRECTION

PATENT NO.   :  5,496,536
DATED        :  March 5, 1996
INVENTOR(S)  :  Gerald Wolf It is certified that error appears in the above-indentified patent and that said Letters Patent is hereby corrected as shown below:

Column 13, Line 35, change "Valley, Pa.).)" to Valley, PA).--.

Column 14, Line 47, change "injection were days" to --injection were 3 days--.

Column 15, Line 4, change "EXAMPLE VI" to --EXAMPLE IV--.

Column 15, Line 26, change "our Signal systems" to --our Signa systems--.

Column 15, Line 29, change "EXAMPLE V" to --EXAMPLE VI--.

Column 16, Line 24, change "in the lymph" to --lymph--.

Signed and Sealed this

Seventeenth Day of September, 1996

Attest:

BRUCE LEHMAN

*Attesting Officer*          *Commissioner of Patents and Trademarks*